(12) United States Patent
McKinnon et al.

(10) Patent No.: US 8,540,677 B2
(45) Date of Patent: Sep. 24, 2013

(54) VASCULAR ACCESS DEVICE CHAMBER VENTING

(75) Inventors: Austin Jason McKinnon, Herriman, UT (US); Christopher N. Cindrich, Draper, UT (US); Mark A. Crawford, Sandy, UT (US); Weston F. Harding, Lehi, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 737 days.

(21) Appl. No.: 11/931,538

(22) Filed: Oct. 31, 2007

(65) Prior Publication Data

US 2008/0132877 A1 Jun. 5, 2008

Related U.S. Application Data

(60) Provisional application No. 60/864,111, filed on Nov. 2, 2006.

(51) Int. Cl.
*A61M 5/178* (2006.01)

(52) U.S. Cl.
USPC ..................... 604/167.04; 604/236

(58) Field of Classification Search
USPC ........ 604/19, 48, 93.01, 246, 288.01–288.04, 604/164.01, 167.01–167.06, 122, 168.01
See application file for complete search history.

(56) References Cited

U.S. PATENT DOCUMENTS

| | | | |
|---|---|---|---|
| 4,324,239 A | 4/1982 | Gordon et al. | |
| 4,765,588 A | 8/1988 | Atkinson | |
| 4,935,010 A | 6/1990 | Cox et al. | |
| 5,120,313 A * | 6/1992 | Elftman | 604/175 |
| 5,251,873 A | 10/1993 | Atkinson et al. | |
| 5,295,657 A | 3/1994 | Atkinson | |
| 5,295,658 A | 3/1994 | Atkinson et al. | |
| 5,342,316 A | 8/1994 | Wallace | |
| 5,441,487 A | 8/1995 | Vedder | |
| 5,474,544 A | 12/1995 | Lynn | |
| 5,501,426 A | 3/1996 | Atkinson et al. | |
| 5,533,708 A | 7/1996 | Atkinson et al. | |
| 5,549,651 A | 8/1996 | Lynn | |
| 5,738,663 A | 4/1998 | Lopez | |
| 5,957,898 A | 9/1999 | Jepson et al. | |
| 6,171,287 B1 | 1/2001 | Lynn et al. | |
| 6,261,282 B1 | 7/2001 | Jepson et al. | |
| 6,344,033 B1 | 2/2002 | Jepson et al. | |
| 6,428,520 B1 * | 8/2002 | Lopez et al. | 604/249 |
| 6,595,964 B2 | 7/2003 | Finley et al. | |
| 6,635,044 B2 | 10/2003 | Lopez | |

(Continued)

FOREIGN PATENT DOCUMENTS

JP 63-188001 U 12/1988
WO WO 2007/047060 A2 4/2007

*Primary Examiner* — Kevin C Sirmons
*Assistant Examiner* — Imani Hayman
(74) *Attorney, Agent, or Firm* — Jeanne Lukasavage; Craig Metcalf; Kirton McConkie

(57) ABSTRACT

A vascular access device within an external environment may include a body and a septum at least partially housed within the body, a gas chamber housed within the body and the septum, and a vent adjacent the body capable of facilitating gas transfer between the gas chamber and the external environment. A method of venting a gas chamber within a medical device includes transferring gas between the gas chamber and an external environment of the device through a vent that is adjacent the body of the device.

12 Claims, 7 Drawing Sheets

(56) References Cited

U.S. PATENT DOCUMENTS

| | | |
|---|---|---|
| 6,651,956 B2 | 11/2003 | Miller |
| 6,669,681 B2 | 12/2003 | Jepson et al. |
| 6,866,656 B2 | 3/2005 | Tingey et al. |
| 6,908,459 B2 | 6/2005 | Harding et al. |
| 7,025,746 B2 * | 4/2006 | Tal .............................. 604/164.1 |
| 2002/0193752 A1 | 12/2002 | Lynn |
| 2003/0208165 A1 | 11/2003 | Christensen et al. |
| 2004/0138626 A1 | 7/2004 | Cote, Sr. et al. |
| 2004/0199126 A1 * | 10/2004 | Harding et al. ................ 604/256 |
| 2005/0226742 A1 * | 10/2005 | Unger et al. .................. 417/412 |
| 2005/0256500 A1 | 11/2005 | Fujii |
| 2006/0155258 A1 * | 7/2006 | Rogers et al. ................. 604/508 |
| 2008/0108956 A1 * | 5/2008 | Lynn et al. .................... 604/256 |

* cited by examiner

VASCULAR ACCESS DEVICE CHAMBER VENTING

RELATED APPLICATIONS

This application claims the benefit of U.S. Provisional Application No. 60/864,111, filed Nov. 2, 2006, entitled VASCULAR ACCESS DEVICE CHAMBER VENTING, which is incorporated herein by reference.

BACKGROUND OF THE INVENTION

The present disclosure relates to infusion therapy with vascular access devices. Infusion therapy is one of the most common health care procedures. Hospitalized, home care, and other patients receive fluids, pharmaceuticals, and blood products via a vascular access device inserted into the vascular system. Infusion therapy may be used to treat an infection, provide anesthesia or analgesia, provide nutritional support, treat cancerous growths, maintain blood pressure and heart rhythm, or many other clinically significant uses.

Infusion therapy is facilitated by a vascular access device. The vascular access device may access a patient's peripheral or central vasculature. The vascular access device may be indwelling for short term (days), moderate term (weeks), or long term (months to years). The vascular access device may be used for continuous infusion therapy or for intermittent therapy.

A common vascular access device is a plastic catheter that is inserted into a patient's vein. The catheter length may vary from a few centimeters for peripheral access to many centimeters for central access. The catheter may be inserted transcutaneously or may be surgically implanted beneath the patient's skin. The catheter, or any other vascular access device attached thereto, may have a single lumen or multiple lumens for infusion of many fluids simultaneously.

The vascular access device commonly includes a Luer adapter to which other medical devices may be attached. For example, an administration set may be attached to a vascular access device at one end and an intravenous (IV) bag at the other. The administration set is a fluid conduit for the continuous infusion of fluids and pharmaceuticals. Commonly, an IV access device is a vascular access device that may be attached to another vascular access device, closes the vascular access device, and allows for intermittent infusion or injection of fluids and pharmaceuticals. An IV access device may include a housing and a septum for closing the system. The septum may be opened with a blunt cannula or a male Luer of a medical device.

When the septum of a vascular access device fails to operate properly, certain complications may occur. Complications associated with infusion therapy may cause significant morbidity and even mortality. One significant complication is catheter related blood stream infection (CRBSI). An estimate of 250,000-400,000 cases of central venous catheter (CVC) associated BSIs occur annually in US hospitals. Attributable mortality is an estimated 12%-25% for each infection and a cost to the health care system of $25,000-$56,000 per episode.

Current vascular access devices prevent complications, such as infection resulting in CRBSIs, by providing a septum that functions properly during attachment and/or access of the vascular access device by other medical devices. Septa that function properly will act, in part, as infection barriers between the internal and external environments of the vascular access device during attachment and/or access by other medical devices. By functioning properly as infection barriers, septa minimize CRBSI's and other complications.

In order to function properly, a septum needs to open and close during use without difficulty. Often, a gas chamber adjacent a septum, must be vented to permit gas to transfer to an external environment as the septum is actuated during use. If neighboring gas chambers are not vented, a septum will be unable to open without significant force. Once opened, the septum will be reluctant to close as a result of neighboring gas chambers that remain compressed under vacuum pressure. Thus, what are needed are various septum venting structures and methods capable of maximizing proper septum functionality.

BRIEF SUMMARY OF THE INVENTION

The present invention has been developed in response to problems and needs in the art that have not yet been fully resolved by currently available vascular access systems, devices, and methods. Thus, these systems, devices, and methods are developed to reduce complications, such as the risk and occurrence of CRBSIs, by providing septum venting structures and methods that maximize proper septum functionality.

A medical device may include a vascular access device placed within an external environment. The vascular access device may include a body, a septum at least partially housed within the body, a gas chamber housed between the body and the septum, and a vent adjacent the body. The vent facilitates gas transfer between the gas chamber and the external environment.

The vent may be formed within at least a portion of the septum. For example, the septum may include a bottom disc and the vent may be a channel formed within the top surface of the bottom disc of the septum. As another example, the septum may include a top disc, and the vent may be a channel formed through the top disc of the septum. Alternately, the vent may be a channel formed on the bottom surface of the top disc of the septum.

The vent may also be a non-compressible gas channel that is situated between the septum and the body. The non-compressible gas channel may include a porous material. The vent may also be a low pressure gas valve adjacent the body. In addition, the body may be a frame, and the vent may transfer gas between the frame members to the external environment of the device.

A method of venting a gas chamber within a medical device includes providing a vascular access device in an external environment, providing a vent adjacent the body of the vascular access device, and transferring gas between a gas chamber housed within the body of the device and the external environment through the vent. The device also includes a septum housed within the body, and the gas chamber is located between the body and the septum.

The vent may be formed within at least a portion of the septum. For example, the septum may include a bottom disc and the vent may be a channel formed within the top surface of the bottom disc, and the method may also include transferring gas through the channel of the septum. As another example, the septum may include a top disc and the vent may be a channel formed through the top disc of the septum, and the method may include transferring gas through the septum. As yet another example, the septum may include a top disc and the vent may be a channel formed on the bottom surface of the top disc of the septum, and the method may include transferring gas through the channel of the septum.

The vent may also be a non-compressible gas channel situated between the septum and the body. The vent may also be a low pressure gas valve adjacent the body. The body may also be a frame including multiple windows between both the gas chamber housed within the body and the external environment.

A medical device may include a means for accessing the vascular system of a patient and a means for transferring gas between the means for accessing the vascular system of a patient and an external environment. The means for accessing the vascular system of a patient may include a body, a septum at least partially housed within the body, and a gas chamber between the body and at least a portion of the septum. The means for transferring gas may transfer gas between the gas chamber and an environment that is external to the means for accessing the vascular system of a patient. The means for transferring gas may be formed within at least a portion of the septum. The means for transferring gas may also be adjacent the body.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
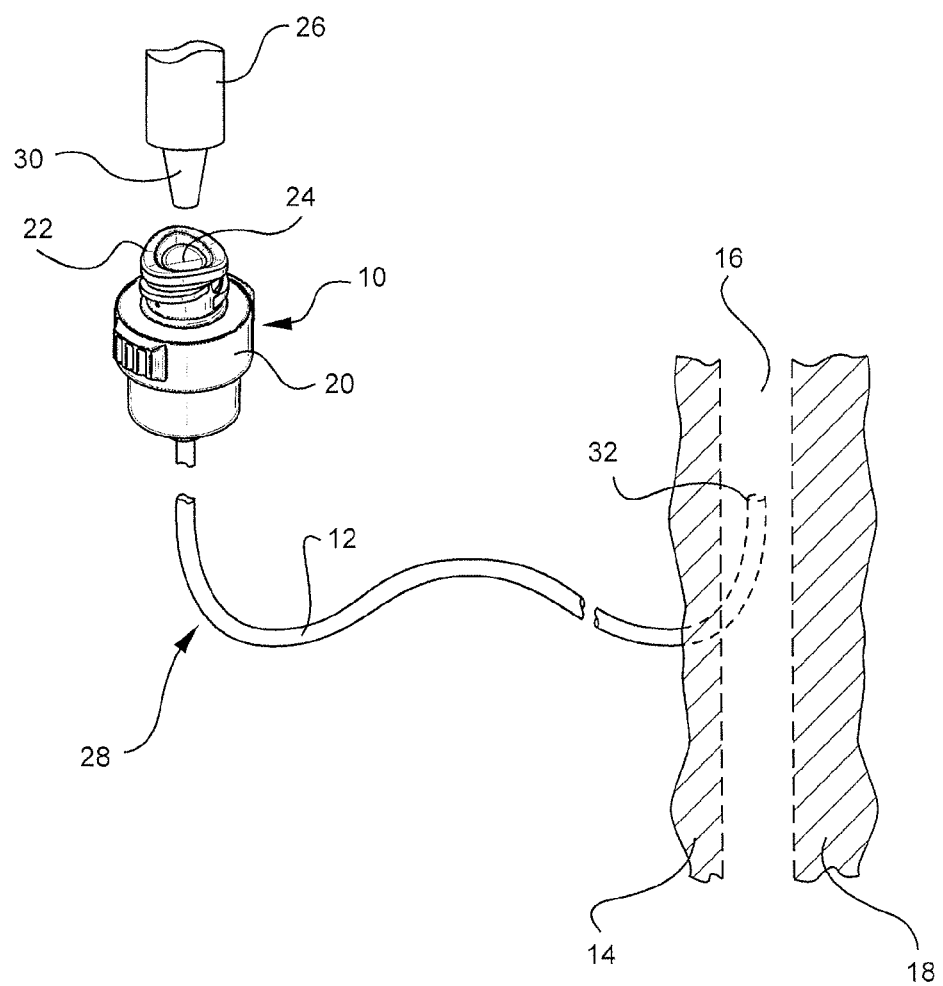
FIG. 1 is a perspective view of an extravascular system connected to the vascular system of a patient.

Referring now to FIG. 1, a vascular access device (also referred to as an extravascular device, intravenous access device, access port, and/or any device attached to or functioning with an extravascular system) 10 is used to introduce a substance via a catheter 12 across the skin 14 and into a blood vessel 16 of a patient 18. The vascular access device 10 includes a body 20 with a lumen and a septum 22 placed within the lumen. The septum 22 has a slit 24 through which a separate extravascular device 26, such as a syringe, may introduce a substance into the vascular access device 10.

The device 10 and all structures used in combination therewith may form a larger extravascular system 28. As part of the system 28, a tip 30 of the separate device 26 may be inserted into the device 10 through the slit 24 of the septum 22. The tip 30 serves to communicate fluid through the device 10 and the end 32 of the catheter 12 when the device 10 is in use. In an embodiment of the invention, as the tip 30 penetrates the device 10, the two opposing slit 24 surfaces of the septum 22 separate in opposing lateral directions and stretch the slit 24 surfaces of the septum 22 in an axial direction, thus increasing the overall height of the septum 22. In this particular embodiment, as the height of the septum is increased, the seal between the device 10 and the tip 30 is rendered more effective.

Figure 2:
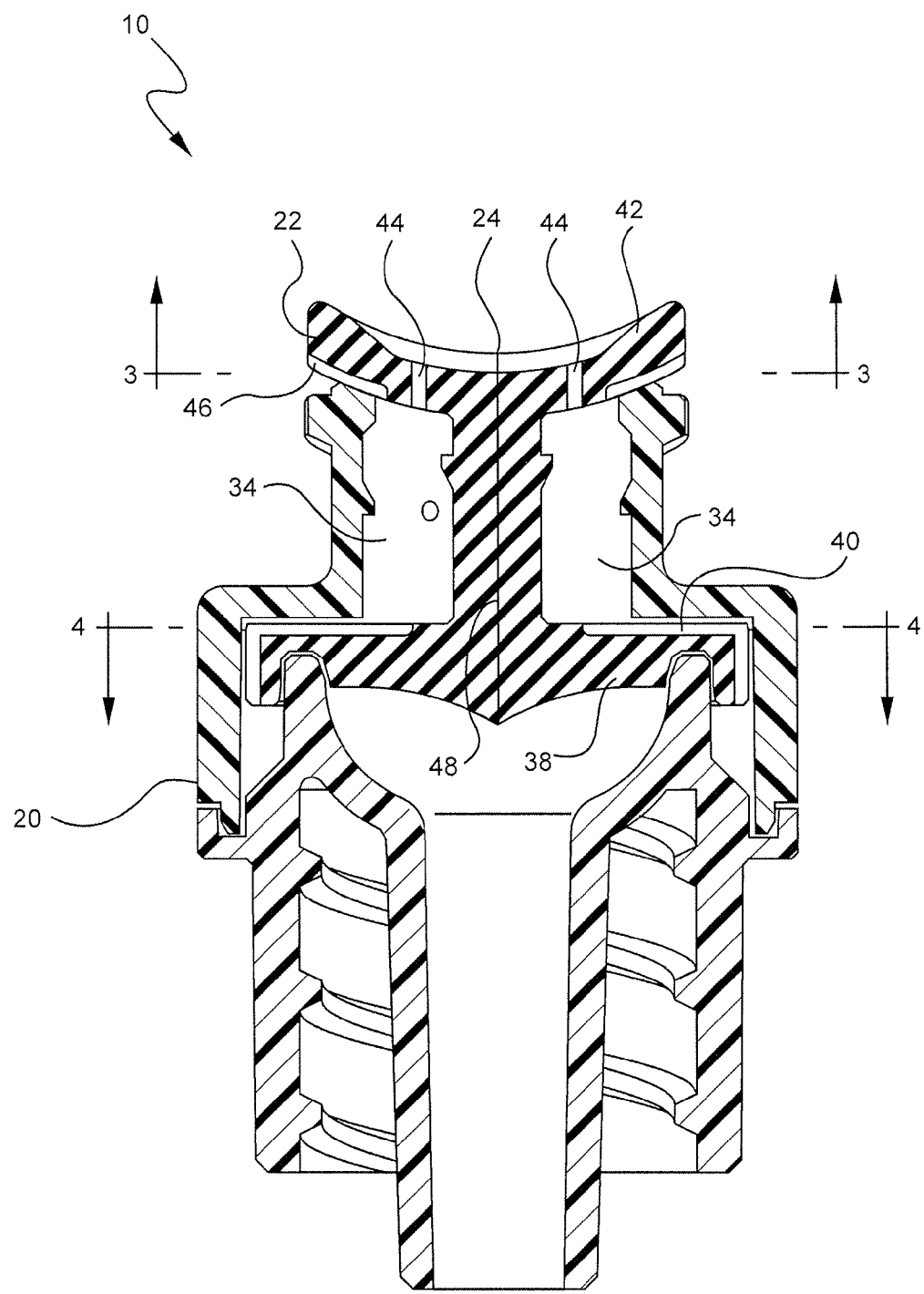
FIG. 2 is a cross section view of a vascular access device having at least one vent.

Referring now to FIG. 2, a vascular access device 10 is used within an external environment and includes a body 20 and a septum 22 at least partially housed within the body 20. A gas chamber 34 is also housed within the body 20, between the body 20 and the septum 22. At least one vent is adjacent the body 20, and the at least one vent facilitates gas transfer between the gas chamber 34 and the external environment 36 of the device 10.

The vent may be formed within at least a portion of the septum 22. The vent may be formed at any point and along any portion of the septum 22. For example, the septum 22 includes a bottom disc 38, and the vent is a channel 40 formed within the top and outer surfaces of the bottom disc 38 of the septum 22. As another example, the septum 22 includes a top disc 42, and the vent is a channel 44 formed through the top disc 42 of the septum 22. As a third example, the vent is a channel 46 formed on the bottom surface of the top disc 42 of the septum 22. Any number of vents, channels, grooves, or other structures capable of transferring gas or facilitating gas transfer between the gas chamber 34 and the external environment 36 through the septum 22 fall within the scope of the embodiments described with reference to FIG. 2.

Figure 3:
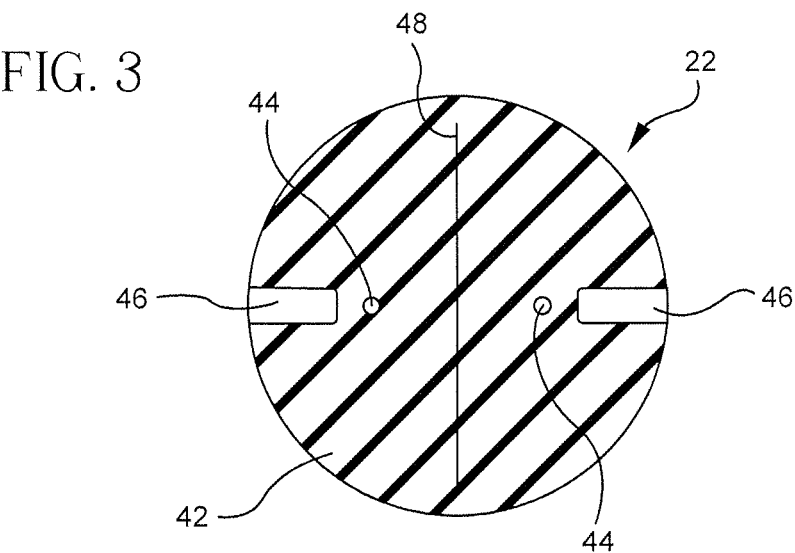
FIG. 3 is a completed cross section view of the vascular access device taken along lines A-A of FIG. 2.

Referring now to FIG. 3, a completed cross section view taken along lines 3-3 of the septum 22 of the device 10 of FIG. 2 shows the top disc 42. As shown in FIG. 3, the channels 44 and 46 are capable of transferring gas between the gas chamber 34 and the external environment 36 of the device 10 through the septum 22.

Figure 4:
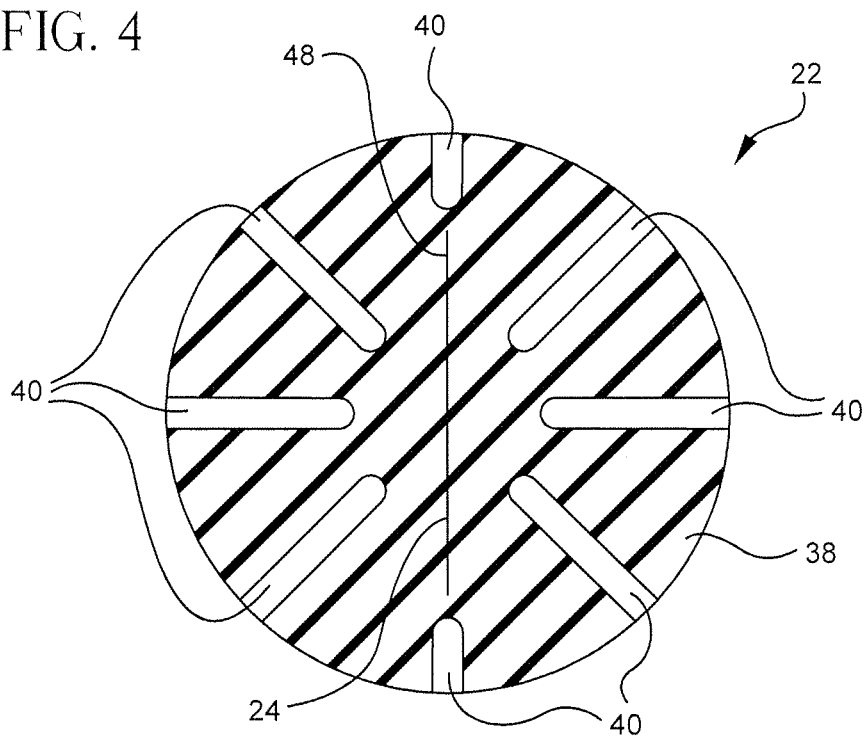
FIG. 4 is a completed cross section view of the vascular access device taken along lines B-B of FIG. 2.

Referring now to FIG. 4, a completed cross section view taken along lines 4-4 of the septum 22 of the device 10 of FIG. 2 shows the bottom disc 38. As shown in FIG. 4, the top surface of the bottom disc 38 of the septum 22 includes at least one channel 40 capable of facilitating gas transfer between the gas chamber 34 and the external environment 36 through the septum 22.

As the septum 22 of the embodiments described with reference to FIGS. 2 through 4 is actuated, gas may transfer between the gas chamber 34 and the external environment through any chamber or vent. For example, as the tip 30 of a separate access device 26 is inserted into the slit 24 of the septum 22, the two opposing surfaces 48 of the slit 24 will separate in opposite lateral directions towards the body 20 of the device 10, causing one or more gas chambers 34 to decrease in size. As the gas chamber 34 decreases in size, gas will transfer through a vent to the external environment 36. As the tip 30 is removed from the slit 24, the nature of the resilient nature of the septum 22 will cause the two opposing surfaces 48 of the slit 24 to return to their original position, causing at least one gas chamber 34 to increase its size and volume to its original level. As the volume of the gas chamber 34 returns to its original level, gas will travel from the external environment through a vent or channel into the gas chamber 34, thus avoiding any vacuum within the gas chamber 34 that would prevent or inhibit the two opposing surfaces 48 of the slit 24 from returning to their original closed position. Any vent or gas chamber within the septum 22 of the device 10 described with reference to FIGS. 2 through 4 may be carried through any portion of the septum 22, such as the bottom disc 38, directly to the external environment 36 as described with reference to FIG. 5.

Figure 5:
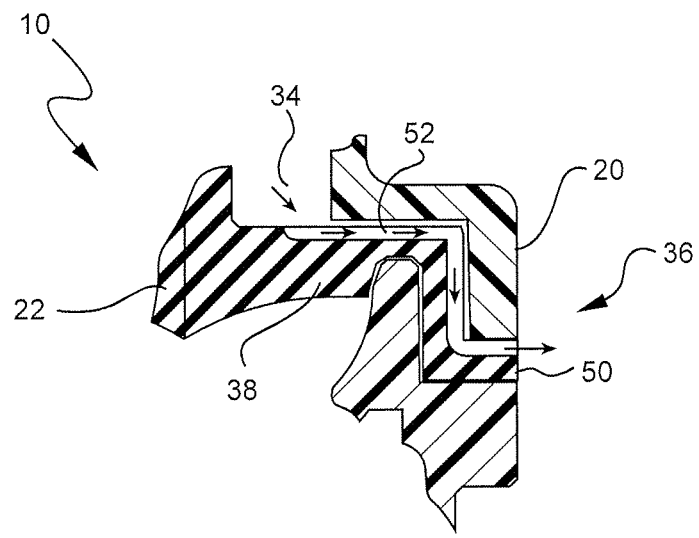
FIG. 5 is a partial close-up, cross section view of a vascular access device having a vent within a septum.

Referring now to FIG. 5, a close-up view of a vascular access device includes a view of the bottom disc 38 of a septum 22. The bottom disc 38 extends its arm 50 from the interior of the body 20 of the device 10 to the external environment 36 surrounding the device 10. The septum 22 is formed of a resilient, elastomeric material and is housed between portions of the body 20 where the arm 50 approaches the external environment 36. A gas chamber 34 housed between the septum 22 and the body 20 communicates with the external environment 36 in a manner that facilitates gas transfer through a vent or continuous channel 52 formed within the top surface of the bottom disc 38. The vent or continuous channel 52 provides continuous air supply from the gas chamber 34 to the external environment 36 during use of the device 10. Thus, in a manner similar to the embodiments described with reference to FIGS. 2 through 4, the embodiment described with reference to FIG. 5 permits and facilitates gas transfer between the gas chamber 34 and the external environment 36 during septum 22 actuation.

Figure 6:
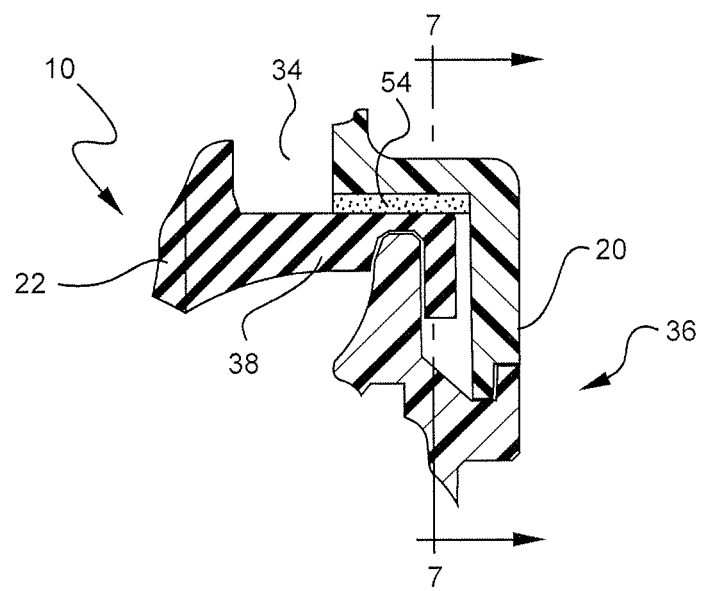
FIG. 6 is partial close-up cross section view of a vascular access device having a non-compressible gas channel.

Referring now to FIG. 6, a close-up, partial cross section view of a vascular access device 10 includes a non-compressible gas channel 54 housed or otherwise situated between the bottom disc 38 of the septum 22 and the body 20 of the device 10. The non-compressible gas channel 54 may be formed of any material that is non-deformable and non-compressible and capable of transferring gas through its porous structure or material. The non-compressible gas channel 54 may be situated at any point between any portion of the septum 22 and the body 20 in order to provide a path of gas transfer from the gas chamber 34 and any other chamber within the device 10 and/or the external environment 36.

Figure 7:
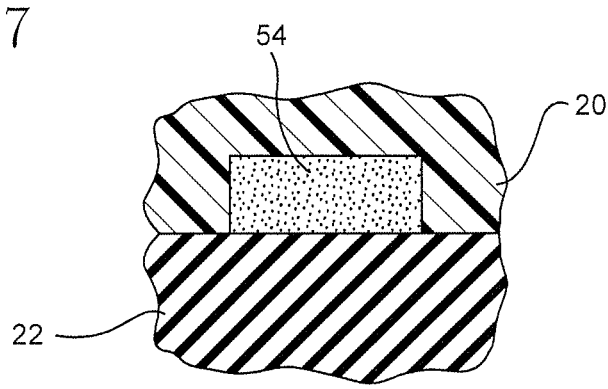
FIG. 7 is partial cross section view of the non-compressible gas channel taken along lines A-A of FIG. 6.

Referring now to FIG. 7, a partial cross section view of a portion of the device 10 of FIG. 6 taken along lines 7-7 shows the non-compressible gas channel 54. As shown in FIG. 7, the non-compressible gas channel 54 is situated between the septum 22 and the rigid housing of the body 20. The non-compressible gas channel 54 may extend to the external environment 36 as shown, for example, by the arm 50 of FIG. 5.

Figure 8:
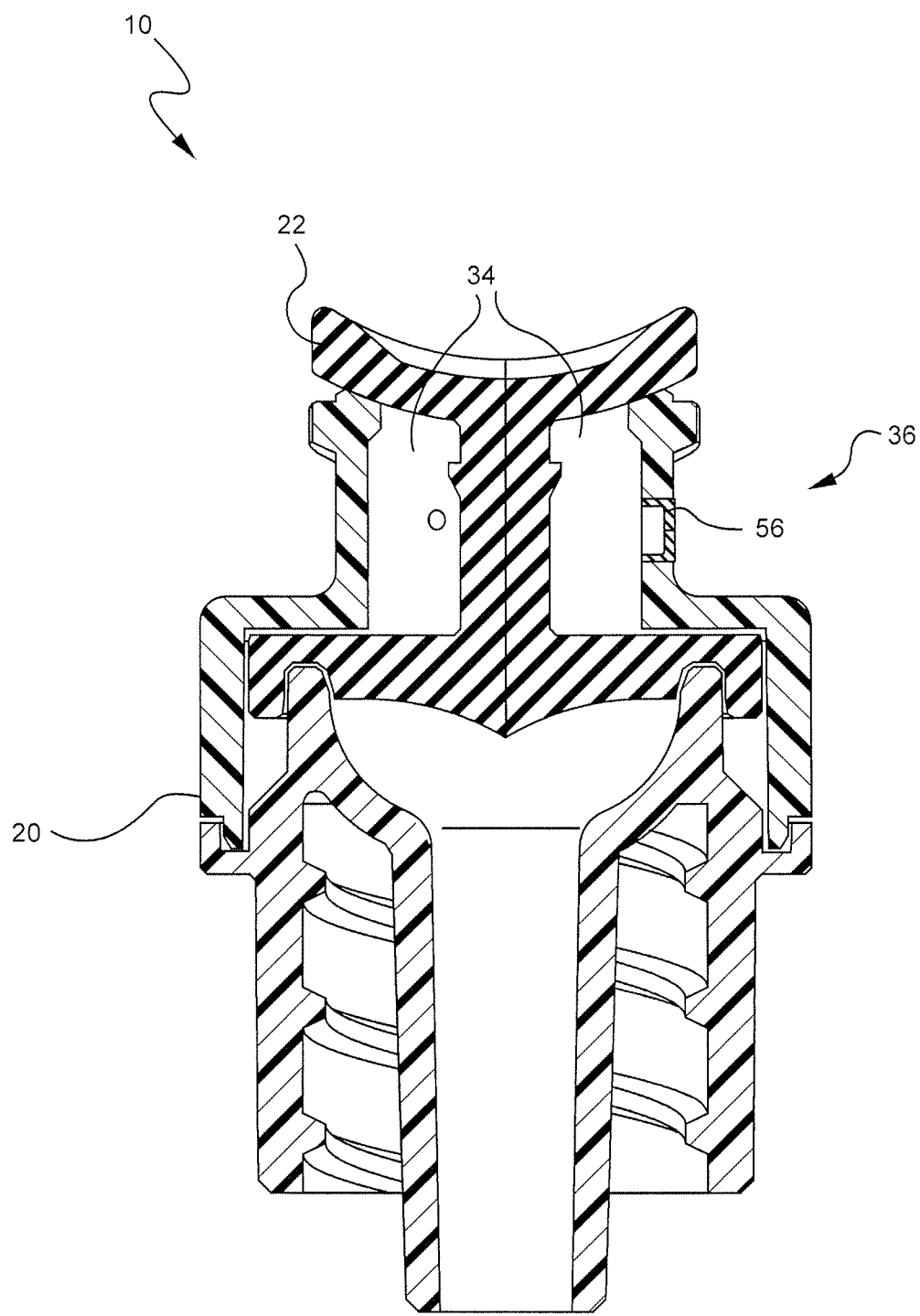
FIG. 8 is a cross section view of a vascular access device with a gas valve.
Figure 8A:
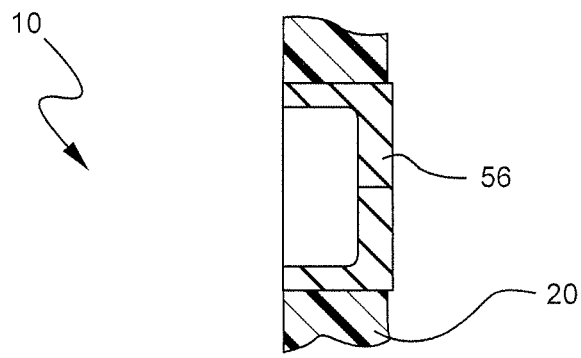
FIG. 8A is a cross section view of the gas value of FIG. 8.
Figure 8B:
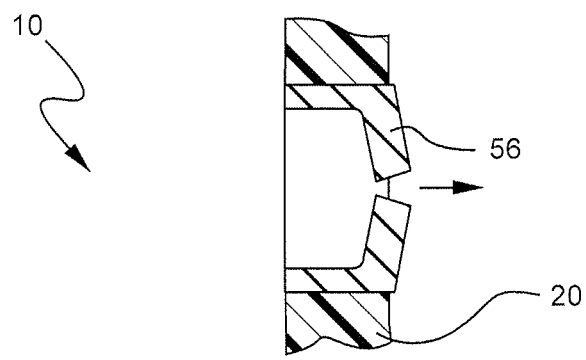
FIG. 8B is a cross section view of the gas value of FIG. 8.
Figure 8C:
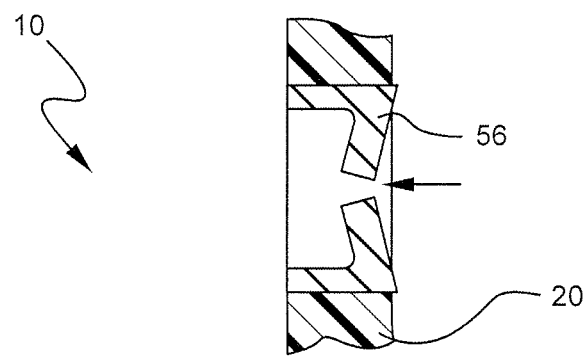
FIG. 8C is a cross section view of the gas value of FIG. 8.

Referring now to FIG. 8, a vascular access device 10 may include a low pressure gas valve 56 located adjacent the body 20 of the device 10. The low pressure bidirectional gas valve 56 remains closed when the device 10 is not in use, leaving no open channel for gas transfer between the gas chamber 34 of the device 10 and the external environment 36. As the device 10 is used and the septum 22 is actuated, the gas valve 56 opens allowing gas to escape the gas chamber 34 into the external environment 36. When the septum 22 returns to its original position after actuation, for example, upon removal of the tip 30 of a separate access device 26, the bidirectional gas valve 56 will permit gas to enter the gas chamber 34 from the external environment 36. The gas valve 56 remains closed between accesses of the device 10 as shown in FIG. 8A. The gas valve 56 permits gas to escape from the chamber 34 during insertion of a device into the septum 22 as shown in FIG. 8B. And, the gas valve 56 permits gas to enter the gas chamber 34 upon removal of a device accessing the septum 22 as shown in FIG. 8C.

Figure 9:
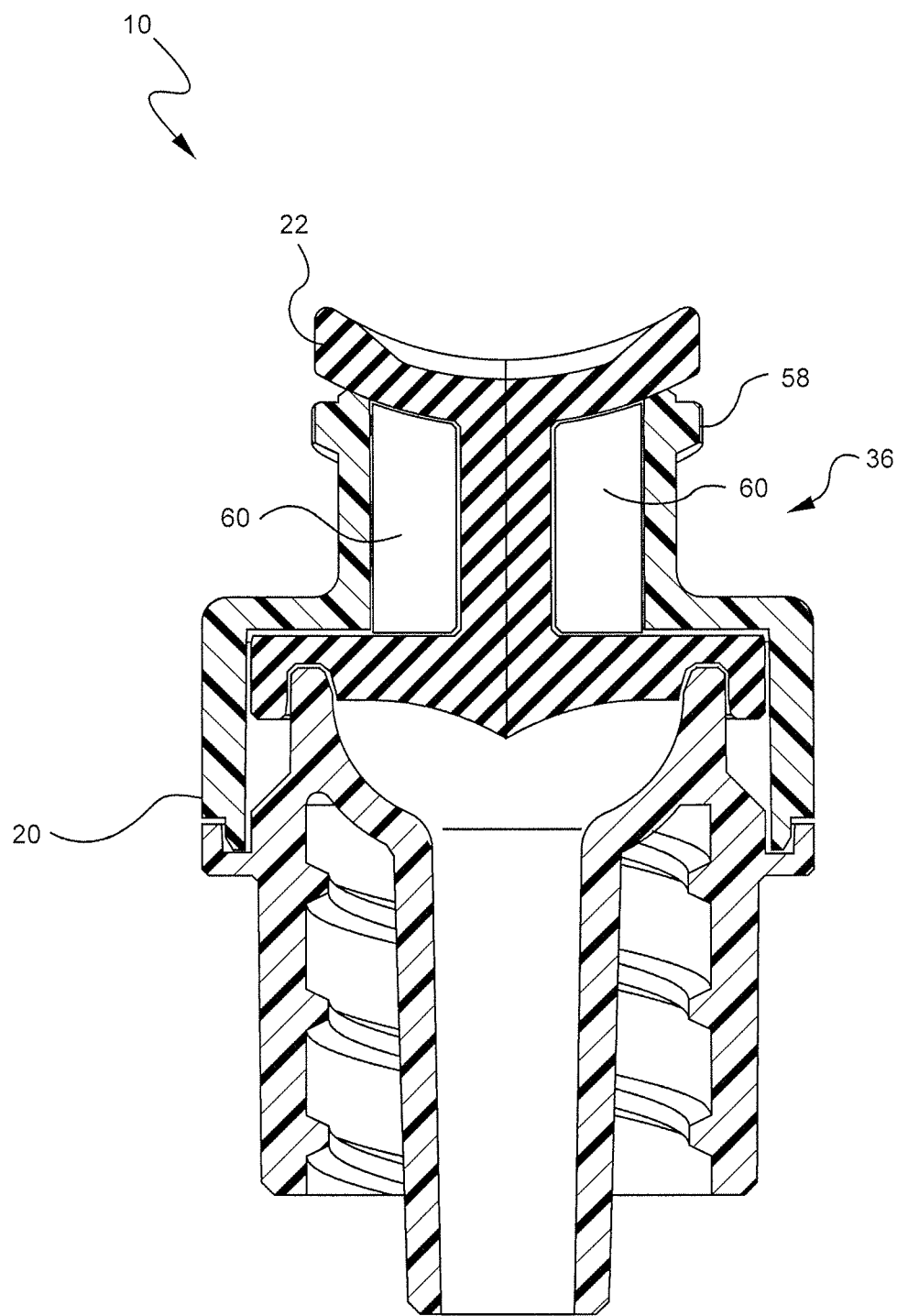
FIG. 9 is a cross section view of a vascular access device with a framed body.

Referring now to FIG. 9, a vascular access device 10 includes a body 20 that is a frame that provides only the support necessary to provide the structure for proper septum 22 functionality and proper attachment to a separate access device 26 by means of threads 58 that are attached to the frame of the body 20. Thus, large windows 60 in the frame of the body 20 appear where the gas chamber 34 would normally have appeared in the embodiments previously described. Thus, the windows 60 operate as vents that transfer gas between the frame members of the body 20, providing means whereby gas may exchange between any internal gas chamber and the external environment 36.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A medical device, comprising:
    a vascular access device within an external environment, wherein the vascular access device includes a body;
    a septum at least partially housed within the body, the septum having a generally I-shaped cross section including a top portion and a bottom portion, the top and bottom portions being interconnected via a middle portion, the septum having a slit;
    a gas chamber forming a void between the body and the middle portion of the septum; and
    a vent providing fluid communication between the gas chamber and the external environment wherein the vent includes a channel formed within at least a portion of the septum and further comprising a low pressure gas valve adjacent the body.

2. The medical device of claim 1, wherein the vent comprises a portion of the bottom portion of the septum.

3. The medical device of claim 1, wherein the vent comprises a portion of the top portion of the septum.

4. The medical device of claim 1, wherein the channel of the vent further comprises a non-compressible gas channel situated between the septum and the body.

5. The medical device of claim 4, wherein the non-compressible gas channel includes a porous material.

6. The medical device of claim 1, wherein the body is a frame comprising a plurality of frame members, and wherein the vent transfers gas between the plurality of frame members.

7. A method of venting a gas chamber within a medical device, comprising:

providing a vascular access device in an external environment, wherein the device includes a body, a septum housed within the body, the septum having a generally I-shaped cross section including a top portion and a bottom portion, the top and bottom portions being interconnected via a middle portion, and a gas chamber forming a void between the body and the middle portion of the septum, the septum having a slit;

providing fluid communication between the gas chamber and the external environment by a vent comprising a low pressure gas valve adjacent the body; and transferring a gas between the gas chamber and the external environment via the vent.

8. The method of claim 7, wherein the medical device further comprises a channel forming a portion of the septum.

9. The method of claim 7, wherein the medical device further comprises a channel forming a portion of the top portion of the septum.

10. The method of claim 7, wherein the medical device further comprises a channel forming a portion of the bottom portion of the septum.

11. The method of claim 7, wherein the vent further comprises a non-compressible gas channel situated between the septum and the body.

12. The method of claim 7, wherein the body is a frame comprising a plurality of frame members, and wherein a portion of the vent further comprises a pathway between adjacent frame members.

* * * * *